(12) United States Patent
Park et al.

(10) Patent No.: US 11,817,184 B2
(45) Date of Patent: Nov. 14, 2023

(54) GRAPH NEURAL NETWORK FORCE FIELD COMPUTATIONAL ALGORITHMS FOR MOLECULAR DYNAMICS COMPUTER SIMULATIONS

(71) Applicant: Robert Bosch GmbH, Stuttgart (DE)

(72) Inventors: Cheol Woo Park, Evanston, IL (US); Jonathan Mailoa, Cambridge, MA (US); Mordechai Kornbluth, Brighton, MA (US); Georgy Samsonidze, San Francisco, CA (US); Soo Kim, Cambridge, MA (US); Karim Gadelrab, Boston, MA (US); Boris Kozinsky, Waban, MA (US); Nathan Craig, Santa Clara, CA (US)

(73) Assignee: Robert Bosch GmbH, Stuttgart (DE)

( * ) Notice: Subject to any disclaimer, the term of this patent is extended or adjusted under 35 U.S.C. 154(b) by 1166 days.

(21) Appl. No.: 16/414,260

(22) Filed: May 16, 2019

(65) Prior Publication Data

US 2020/0365236 A1    Nov. 19, 2020

(51) Int. Cl.
*G06N 3/08*    (2023.01)
*G06N 3/04*    (2023.01)
*G16C 20/10*    (2019.01)

(52) U.S. Cl.
CPC ............... *G16C 20/10* (2019.02); *G06N 3/04* (2013.01); *G06N 3/08* (2013.01)

(58) Field of Classification Search
CPC ... G06N 3/08; G06N 3/04; G06N 3/06; G16C 20/10; G16C 20/00
See application file for complete search history.

(56) References Cited

U.S. PATENT DOCUMENTS

| | | | |
|---|---|---|---|
| 2018/0137155 A1* | 5/2018 | Majumdar | ............. G06N 10/00 |
| 2019/0272468 A1* | 9/2019 | Feinberg | ................ G06N 3/126 |

FOREIGN PATENT DOCUMENTS

CN    109461475 A    3/2019

OTHER PUBLICATIONS

Prates et al., "Typed Graph Networks," Feb. 24, 2019 (Year: 2019).*
Bojchevski et al., "Deep Gaussian Embedding of Graphs: Unsupervised Inductive Learning via Ranking," Feb. 27, 2018 (Year: 2018).*

(Continued)

*Primary Examiner* — Kamran Afshar
*Assistant Examiner* — Brian J Hales
(74) *Attorney, Agent, or Firm* — Brooks Kushman P.C.

(57) ABSTRACT

A computational method simulating the motion of elements within a multi-element system using a graph neural network (GNN). The method includes converting a molecular dynamics snapshot of the elements into a directed graph comprised of nodes and edges. The method further includes the step of initially embedding the nodes and the edges to obtain initially embedded nodes and edges. The method also includes updating the initially embedded nodes and edges by passing a first message from a first edge to a first node using a first message function and passing a second message from the first node to the first edge using a second message function to obtain updated embedded nodes and edges, and predicting a force vector for one or more elements based on the updated embedded edges and a unit vector pointing from the first node to a second node or the second node to the first node.

20 Claims, 7 Drawing Sheets

(56) References Cited

OTHER PUBLICATIONS

Behler, Atom-Centered Symmetry Functions for Constructing High-Dimensional Neural Network Potentials, The Journal of Chemical Physics, Feb. 16, 2011, AIP Publishing, Germany, DOI: 10.1063/1.3553717, 14 pages.

Xie et al., Crystal Graph Convolutional Neural Networks for an Accurate and Interpretable Prediction of Material Properties, Physical Review Letters, Apr. 6, 2018, Massachusetts, DOI: 10.1103/PhysRevLett.120.145301, 7 pages.

Li et al., Gated Graph Sequence Neural Networks, Published as a conference paper at ICLR 2016, Sep. 22, 2017, Canada, 20 pages.

Behler et al., Generalized Neural-Network Representation of High-Dimensional Potential-Energy Surfaces, Physical Review Letters, Apr. 2, 2007, Switzerland, DOI: 10.1103/PhysRevLett.98.146401, 4 pages.

Chen et al., Graph Networks as a Universal Machine Learning Framework for Molecules and Crystals, Feb. 28, 2019, California, 29 pages.

Gastegger et al., High-Dimensional Neural Network Potentials for Organic Reactions and an Improved Training Algorithm, Journal of Chemical Theory and Computation, Apr. 16, 2015, Austria, 12 pages.

Gilmer et al., Neural Message Passing for Quantum Chemistry, Jun. 12, 2017, Australia, 14 pages.

Li et al., Study of Li Atom diffusion in amorphous Li3PO4 with Neural Network Potential, The Journal of Chemical Physics, Dec. 5, 2017, AIP Publishing, Germany, DOI: 10.1063/1.4997242, 11 pages.

Scarselli et al., The Graph Neural Network Model, IEEE Transactions on Neural Networks, vol. 20, No. 1, Jan. 2009, 20 pages.

Cho et al., Three-Dimensionally Embedded Graph Convolutional Network (3DGCN) for Molecule Interpretation, Dec. 4, 2018, Korea, 15 pages.

* cited by examiner

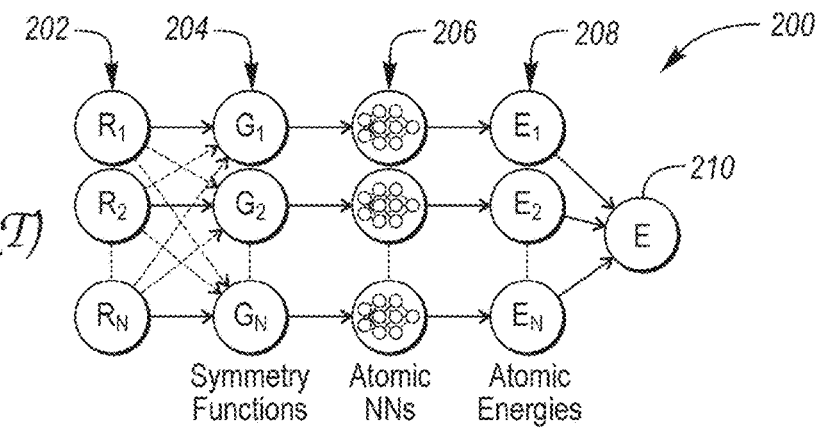
FIG. 2 (PRIOR ART)
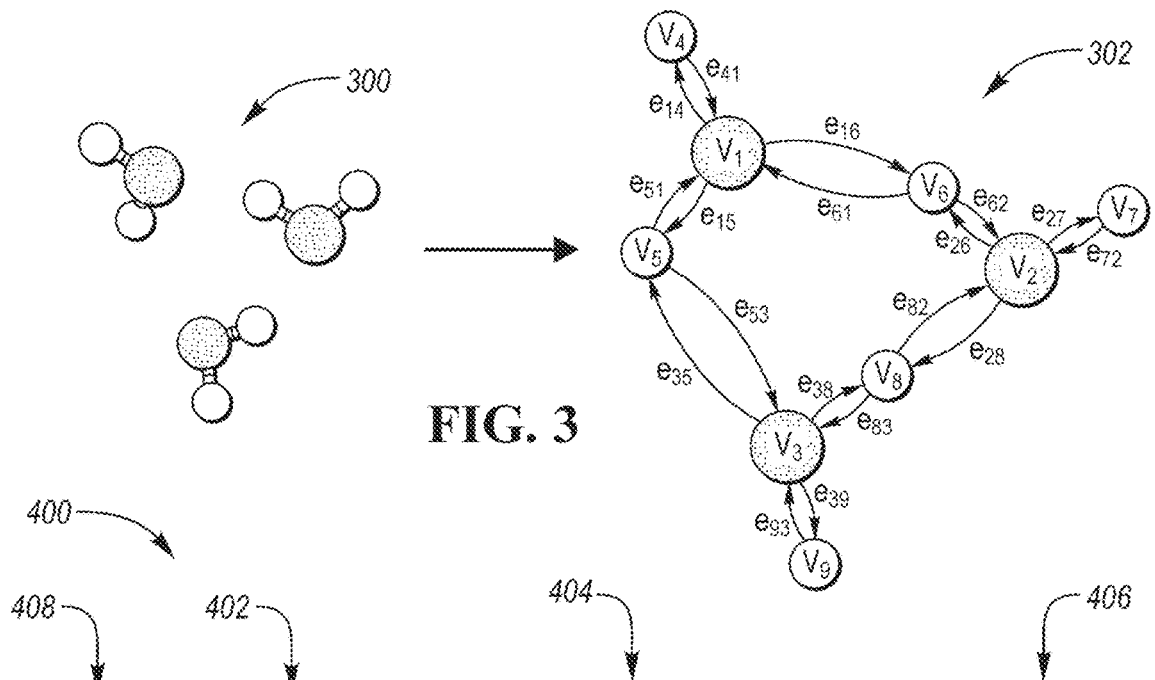
FIG. 3
FIG. 4

GRAPH NEURAL NETWORK FORCE FIELD COMPUTATIONAL ALGORITHMS FOR MOLECULAR DYNAMICS COMPUTER SIMULATIONS

TECHNICAL FIELD

This invention relates generally to graph neural network (GNN) force field computational algorithms for direct prediction of atomic forces in molecular dynamics computer simulations in material systems, such as electrochemical and water filtration devices.

BACKGROUND

Molecular dynamics is a computational materials science methodology for simulating the motion of atoms in a material system at real operating pressure and temperature conditions. Methodologies exist to calculate the underlying atomic forces used in the simulation of the motion of atoms. One methodology is the ab-initio quantum mechanics approach. This approach is very accurate but is also very expensive because of the tremendous amount of computational resources necessary to apply the approach. While other approaches exist that consume less computational resources, these other approaches do not deliver as much accuracy.

SUMMARY

According to one embodiment, a computational method for simulating the motion of elements within a multi-element system using a graph neural network (GNN) is disclosed. The method includes converting a molecular dynamics snapshot of the elements within the multi-element system into a directed graph comprised of nodes and edges. The nodes include first and second nodes and the edges include first and second edges. The method further includes the step of initially embedding the nodes and the edges to obtain initially embedded nodes and edges. The method also includes updating the initially embedded nodes and edges by passing a first message from the first edge to the first node using a first message function and passing a second message from the first node to the first edge using a second message function to obtain updated embedded nodes and edges. The method also includes predicting a force vector for one or more elements within the multi-element system based on the updated embedded edges and a unit vector pointing from the first node to the second node or the second node to the first node.

According to another embodiment, a computational method for simulating the motion of elements within a multi-element system using a graph neural network (GNN) is disclosed. The method includes converting a molecular dynamics snapshot of the elements within the multi-element system into a directed graph comprised of nodes and edges. The nodes include first, second and third nodes and the edges including first, second and third edges. The method further includes initially embedding the nodes and the edges to obtain initially embedded nodes and edges. The method also includes updating the initially embedded nodes and edges by passing a first message from the first edge to the first node using a first message function and passing a second message from the first node to the first edge using a second message function to obtain updated embedded nodes and edges. The second message function represents interactions between the first, second and third nodes. The method also includes predicting a force vector for one or more elements within the multi-element system based on the updated embedded edges.

According to yet another embodiment, a computational method for simulating the motion of elements within a multi-element system using a graph neural network (GNN) is disclosed. The method includes converting a molecular dynamics snapshot of the elements within the multi-element system into a directed graph comprised of nodes and edges. The nodes include first and second nodes and the edges include first and second edges. The method further includes initially embedding the nodes and the edges to obtain initially embedded nodes and edges. The method also includes updating the initially embedded nodes and edges by iteratively passing a first message from the first edge to the first node using a first message function and iteratively passing a second message from the first node to the first edge using a second message function to obtain updated embedded nodes and edges. The method also includes predicting a force vector for one or more elements within the multi-element system based on the updated embedded edges.

BRIEF DESCRIPTION OF THE DRAWINGS

FIG. 2 is a neural network node schematic diagram of a neural network force field (NNFF) energy prediction scheme under the prior art Behler-Parrinello approach.

FIG. 3 is a schematic view depicting an MD snapshot as a directed graph according to one embodiment.

FIG. 4 is a schematic view of GNN including an embedding part, a message-passing part and a force vector calculation part according to one embodiment.

DETAILED DESCRIPTION

Figure 1:
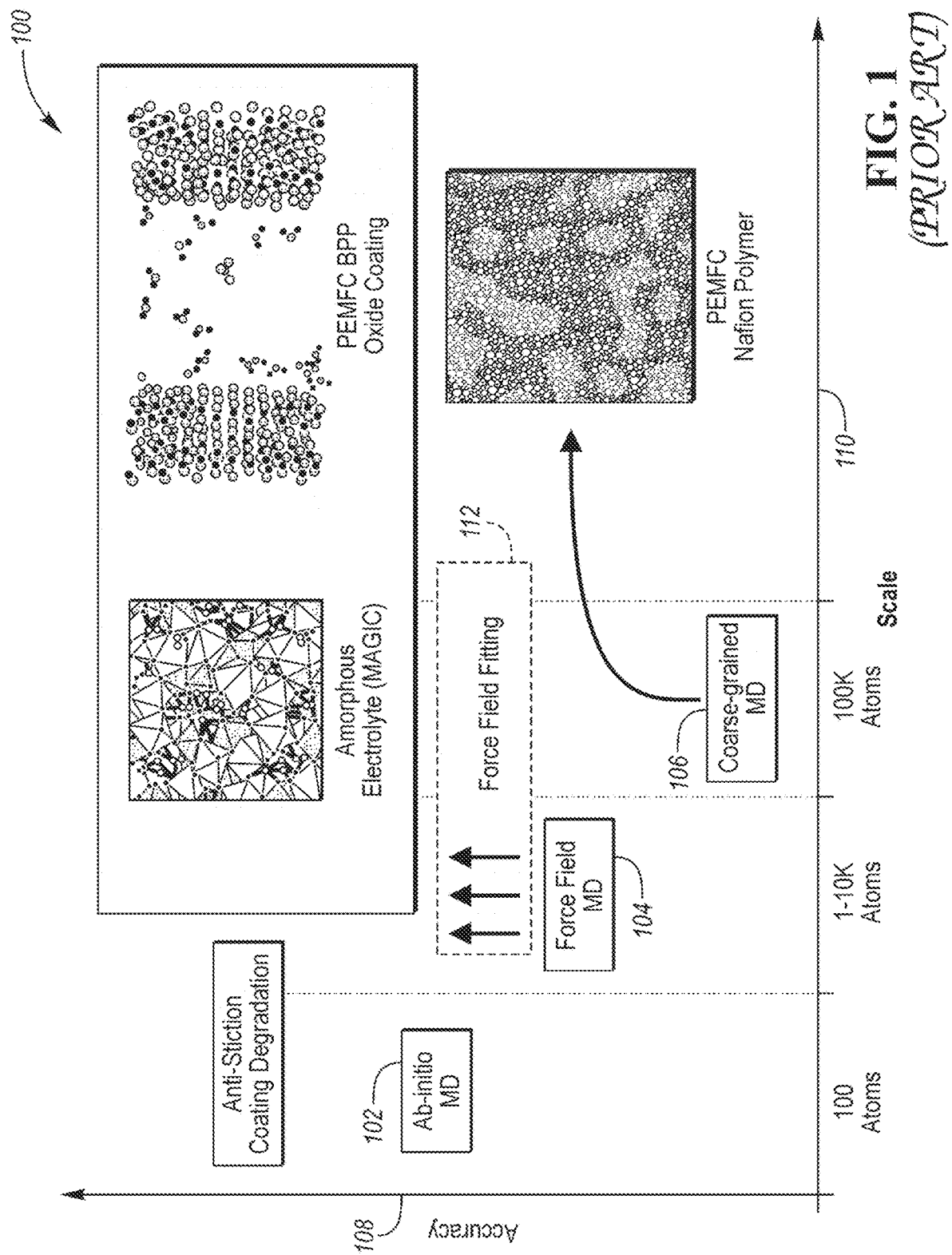
FIG. 1 depicts a schematic graph showing the tradeoff between scale and accuracy for different prior art molecular dynamics (MD) force calculation methods.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The term "substantially" may be used herein to describe disclosed or claimed embodiments. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

Molecular dynamics (MDs) methodologies are beneficial for studying physical phenomena, such as, but not limited to, ionic transport, chemical reactions, and material bulk and surface degradation in material systems, such as, devices or functional materials. Non-limiting examples of such material systems include fuel cells, surface coatings, batteries, water desalination, and water filtration. Methodologies exist to calculate the underlying atomic forces used in the simulation of the motion of atoms. The ab-initio quantum mechanics approach is very accurate but is also very expensive because of the tremendous amount of computational resources necessary to apply the approach.

Neural networks have been utilized to fit and predict quantum mechanics energies. These methodologies have been referred to as neural network force fields (NNFF). Derivatives of energy with respect to atomic positions and forces are predicted using quantum mechanics energies. However, these methodologies are also computationally extensive. In light of the foregoing, what is needed is a computational methodology for calculating atomic forces that delivers an adequate level of accuracy while consuming a reasonable amount of computing resources.

Molecular dynamics use atomic positions (and possibly charges, bonds, or other structural information) to calculate interatomic forces of each atom, which are consequently used to modify the velocities of atoms in the simulation. The resulting trajectories of the atoms are utilized to describe physical phenomena, such as, but not limited to ionic transport in batteries and fuel cells, chemical reactions during bulk and surface material degradation, and solid-state material phase change. A tradeoff exists between the accuracy and size (measured by number of atoms and simulated dynamics time) of the simulation depending on the underlying method used to calculate the atomic forces. As set forth above, one accurate but expensive method uses the ab-initio quantum mechanics approach, known as ab-initio molecular dynamics (AIMD).

FIG. 1 depicts schematic graph 100 showing the tradeoff between scale and accuracy for different prior art MD force calculation methods, e.g., AIMD 102, force field MD 104, and coarse-grained MD 106. The y-axis 108 is accuracy and the x-axis 110 is scale (e.g., 100 atoms, 1-10K atoms and 100K atoms). AIMD 102 can be utilized to model anti-stiction coating degradation. Through force field fitting 112, force field MD can be utilized to model amorphous electrolytes and proton-exchange membrane fuel cells (PEMFC) bi polar plate (BPP) oxide coatings. Coarse grained MD 106 can be utilized to model PEMFC nafion polymers.

AIMD is too computationally demanding for many relevant applications. For instance, according to one estimation, an AIMD simulation on a high-performance computer with two hundred (200) cores would take sixty-five (65) years to complete to study the dynamics behavior of amorphous lithium phosphate glass with about five hundred (500) atoms for five hundred (500) nanoseconds.

An alternative to AIMD is classical molecular dynamics. Using this alternative, interatomic forces have been fitted into some closed functional forms to enable several orders of magnitude speedup over AIMD. This alternative approach has been used to simulate large systems, such as polymers and amorphous materials. According to one estimation, the same simulation identified above using the classical molecular dynamics approach finishes in under two (2) days.

One of the drawbacks of the classical molecular dynamics model using pre-defined functional forms is that they restrict the behavior of interatomic interactions within assumptions that remain valid under certain conditions. For example, a classical force field with quadratic functional forms for the bond between atoms assumes that the chemical bond between atoms do not break. This assumption is contrary to the behavior of nature where chemical bonds in molecules form and break during chemical reactions. Relatively more complex pre-assumed functional forms for simulating chemical reactions exist. For example, reactive force fields, such as ReaxFF, is one such model. These models suffer from the disadvantage of being difficult to parametrize and require a large number of relatively complex handcrafted, closed functional forms.

As described above, NNFF algorithms exist that require the computation of quantum mechanics energies. One implementation of NNFF uses rotation-invariant features developed by Behler and Parrinello (otherwise referred to as the Behler-Parrinello approach), as described in the following articles: J. Behler and M. Parrinello, "Generalized Neural-Network Representation of High-Dimensional Potential-Energy Surfaces", Phys. Rev. Lett. 98, 146401 (2007); M. Gastegger, J. Behler, and P. Marquetand, "Machine Learning Molecular Dynamics for Simulation of Infrared Spectra", Chem. Sci. 2017, 8, 6924; and J. Behler, "Atom-centered Symmetry Functions for Constructing High-Dimensional Neural Network Potentials", J. Chem. Phys., 134, 074106 (2011), all of which are incorporated by reference in their entirety herein.

In this implementation, atoms surrounding central atom i within a predefined radius $R_c$ are used as inputs into the neural network. Instead of using atomic Cartesian coordinates of the atoms as the input features, the atomic Cartesian coordinates are converted into fingerprint feature vectors. These vectors are invariant under physical operations that should not change the energy coordinates of the local atomic structure. These physical operations include rotation, translation, and permutation. Rotation-invariance refers to the energy invariance upon rotating the entire Cartesian coordinates of the local atomic environment by an identical rotation with respect to an arbitrary point in space, such as the central atom i. Translational-invariance refers to the energy invariance upon shifting the entire Cartesian coordinates of the local atomic environment by an identical displacement. Permutation-invariance refers to the energy invariance upon changing the ordering sequence of the atoms in the local atomic environment and keeping their positions fixed. In addition to satisfying these three (3) conditions, the chosen fingerprint feature vectors may also satisfy the following criteria (which are assumed to be consistent with the physics of the system): decaying contribution from atoms further away from the central atom i (down to 0 for $R > R_c$); and smoothly varying as the atomic positions vary smoothly in the local atomic environment.

In one implementation, these five (5) requirements are accomplished by converting a list of atomic coordinates surrounding a central atom i $\{\vec{R_i}\}$ into fingerprint feature vectors $\{\vec{G}_i\}$ described by two-body and three-body functions. Some non-limiting examples of fingerprint functions are listed below:

$$G_i^1 = \sum_j f_c(R_{ij}) \quad (1)$$

$$G_i^2 = \sum_j e^{-\eta(R_{ij}-R_s)^2} \cdot f_c(R_{ij}) \quad (2)$$

$$G_i^3 = \sum_j \cos(\kappa R_{ij}) \cdot f_c(R_{ij}) \quad (3)$$

$$G_i^4 = 2^{1-\zeta} \sum_{j,k\neq i}^{all} (1+\lambda\cos\theta_{ijk})^\zeta \cdot e^{-\eta(R_{ij}^2+R_{ik}^2+R_{jk}^2)} \cdot f_c(R_{ij}) \cdot f_c(R_{ik}) \cdot f_c(R_{jk}) \quad (4)$$

$$G_i^5 = 2^{1-\zeta} \sum_{j,k\neq i}^{all} (1+\lambda\cos\theta_{ijk})^\zeta \cdot e^{-\eta(R_{ij}^2+R_{ik}^2)} \cdot f_c(R_{ij}) \cdot f_c(R_{ik}) \quad (5)$$

where $\eta$, $\kappa$, $\zeta$, and $\lambda$ are user-defined parameters of G fingerprint functions as described in J. Behler, "Atom-centered Symmetry Functions for Constructing High-Dimensional Neural Network Potentials", J. Chem. Phys., 134, 074106 (2011). The values of these parameters are typically chosen to appropriately cover the length-scales relevant for the local atomic system under consideration (typically within a cutoff radius $R_c$<10 A). The cutoff function $f_c$ depends on $R_c$ and can be defined as follows:

$$f_c(R_{ij}) = \begin{cases} 0.5 \cdot \left[\cos\left(\frac{\pi R_{ij}}{R_c}\right)+1\right] & \text{for } R_{ij} \leq R_c \\ 0 & \text{for } R_{ij} > R_c \end{cases} \quad (6)$$

The permutation-invariance is only true for atoms of the same elements. For example, exchanging a C atom at position 1 and a C atom at position 2 describes two systems with the same physics, and accordingly, the permutation-invariance holds true. As another example, exchanging a C atom at position 1 and an O atom at position 2 describes two systems with different physics, and permutation-invariance does not hold true. Consequently, when multi-element systems are investigated, the summations in the G functions above should only be done for atoms with the same elements (for two-body G's) or same element-pairs (for three-body G's). Given m number of elements in a MD system of interest surrounding a central atom i, m different G's are calculated for each parameterized 2-body function and m(m+1)/2 different G's for each parametrized three-body function. Due to the construction of these functions (including rotational invariance), these functions provide beneficial representations for learning the rotation-invariant nature of quantum mechanics. However, a machine learning system using these invariant features are limited to use to predict rotation-invariant outputs such as energy.

Many methodologies based on quantum mechanics (e.g., density functional-theory) are used to calculate energy E of a system. However, these methodologies cannot conveniently partition the electronic energy into contributions from individual atoms. Accordingly, in one or more embodiments, $\{\vec{G}_i\}$ feature vectors for each atom in a system are calculated and then utilized to train or predict a single scalar quantity of energy E as shown in FIG. 2. FIG. 2 depicts a neural network node schematic diagram of an NNFF energy prediction scheme under the prior art Behler-Parrinello approach. Atomic coordinate environments $R_1$ through $R_N$ 202 are used as inputs, respectively, of NNFF algorithm 200. Atomic coordinate environments $R_1$ through $R_N$ 202 are used to calculate symmetry functions $G_1$ through $G_N$ 204. Each atomic coordinate environment $R_1$ through $R_N$ 202 are interrelated with each symmetry function $G_1$ through $G_N$ 204. Atomic NNs 206 are trained using symmetry functions $G_1$ through $G_N$ 204 to obtain atomic energies 208, which are used to obtain total energy E 210.

The NNFF approach for AIMD applications suffers from one or more limitations. For instance, during a training cycle, each of the atomic NNs (typically one NN for each element) is co-trained to a single energy quantity E, which is tied to the system of interest. Accordingly, the NNs are co-dependent because each needs to be co-used to predict a single energy value E and are only optimized for predicting the exact MD system used in the training set. There are no independent $\{\vec{R}_i\} \rightarrow E_i$ samples that can be included for the training of different MD systems containing local atomic environments similar to $\{\vec{R}_i\}$. Secondly, during MD runtime (force prediction cycle), expensive calculations are performed to calculate the force vector $\vec{F}_i$ on atom i. $\vec{F}_i$ is the derivative of total system energy E with respect to displacement of a single atom $\vec{R}_i$. However, prediction of E requires knowing G for all atoms in the MD system $\{\vec{G}_1, \vec{G}_2, \ldots, \vec{G}_N\}$. Consequently, calculating $\vec{F}_i$ requires calculating the fingerprint vector 3N times, as shown in the equation below.

$$F_{k,\alpha} = -\frac{\partial E}{\partial R_{k,\alpha}} = -\sum_{i=1}^N \frac{\partial E_i}{\partial R_{k,\alpha}} = -\sum_{i=1}^N \sum_{j=1}^{M_i} \frac{\partial E_i}{\partial G_{i,j}} \frac{\partial G_{i,j}}{\partial R_{k,\alpha}} \quad (7)$$

where $\alpha$ indicates the Cartesian x, y, and z axes, N is the total number of atoms in the MD system, and $M_i$ is the total number of fingerprint functions describing atom i. Accordingly, calculating forces for all N atoms in the system grows with $O(N^2)$. In certain implementations, certain algorithm modifications can reduce the number of fingerprint vector calculations to 3P times, where P is the average number of atoms in the local atomic environment of the atoms, reducing the computational cost scale to O(N). Nevertheless, this restriction requires 3P $\{\vec{G}_i\}$ calculations for one $\vec{F}_i$ prediction (P may range from 100 to 400 atoms depending on the chosen $R_c$), as opposed to one $\{\vec{G}_i\}$ calculation in a direct $\vec{F}_i$ prediction. Accordingly, an NNFF algorithm with direct $\vec{F}_i$ prediction can accelerate NNFF-based MD $\vec{F}_i$ calculations by two (2) to three (3) orders of magnitude.

In one or more embodiments, a graph neural network (GNN) is utilized because it does not require manually computing rotationally-invariant features of a local atomic environment to predict atomic forces for an MD simulation. The GNN model architecture may be configured to automatically extract translationally and rotationally-invariant features from an input MD simulation snapshot during a training process.

The computational algorithm of one or more embodiments is configured to perform direct $\{\vec{R}_i\} \rightarrow \vec{F}_i$ prediction for each training sample. Accordingly, $\{\vec{R}_i\} \rightarrow \vec{F}_i$ samples from different sets of systems or materials may be combined for force field training and development. The computational algorithm of one or more algorithms may be practically applied to a relatively large atomic system of an interface between materials A and B. A training set may be created by combining separate smaller structures of material A, material B, and the interface between the two.

The computational algorithm of one or more embodiments may be integrated into an MD simulation engine. This integration may be used to perform accurate MD simulations without using the more expensive AIMD methods. The computational algorithm of one or more embodiments find practical application in the modeling of force vectors for one or more elements within the multi-element systems, such as atom/ion dynamics, chemical reactions in fuel cells, water desalination, catalysis, coatings and batteries.

In one or more embodiments, the force prediction algorithm of one or more embodiments is integrated into MD software. A non-limiting example of suitable MD software is Large-scale Atomic/Molecular Massively Parallel Simulator (LAMMPS). LAMMPS is available from Sandia National Laboratories, located in Albuquerque, New Mexico LAMMPS uses a Message Passing Interface (MPI) for parallel communication. LAMMPS is open-source software, distributed under the terms of the GNU General Public License.

The atomic force prediction algorithm of one or more embodiments utilizes graph neural networks (GNN) that may operate directly on graph-structured data. FIG. 3 is a schematic view depicting MD snapshot 300 as directed graph 302 according to one embodiment. As shown in FIG. 3, MD snapshot 300 depicts three (3) water molecules. Directed graph 302 may be represented as g=(V, ε, U) with node $v_i \in V$ representing a state of constituent atom i, directed edge $e_{ij} \in \varepsilon$ representing an influence atom i has on neighboring atom j, and $\vec{u}_{ij} \in U$ representing a direction of this influence, which a unit vector point from atom i to atom j. The unit vectors are not shown in FIG. 3 for the sake of simplicity. In this embodiment, each node is connected to N of its closest neighbors, where N may be predetermined. The GNN of this embodiment operates on directed graph 302 includes three (3) parts: embedding part, message-passing part, and force vector calculation part.

FIG. 4 is a schematic view of GNN 400 including embedding part 402, message-passing part 404 and force vector calculation part 406. GNN 400 of one or more embodiments may take as input graph representation 302 of MD snapshot 300. Inputs 408 of GNN 400 include node $v_i \in V$, edge $e_{ij} \in \varepsilon$, and unit vector $\vec{u}_{ij} \in U$. In embedding part 402 of GNN 400, node $v_i$ and edge $e_{ij}$ are respectively embedded with initial embedding, $h_i^0$ and $h_{(i,j)}^0$. $h_i^0$ may be given as an output of a neural network, where the input is a one hot encoding vector of the atom type represented by $v_i$. $h_{(i,j)}^0$ may be given by applying a Gaussian filter to a distance between atoms i and j. According to one or more embodiments, the one hot encoding vector may be replaced with any unique representation of an atom's element. The Gaussian filter may be defined by its range and step size. For example, for a range of $r_{min}$ and $r_{max}$ and step size $r_{step}$, the Gaussian filter may be given by array $[r_1, r_2, \ldots, r_n]$ where $r_k = r_{min} + (k-1)r_{step}$, k=1, 2, ..., n, and k=1, 2, ..., n. When applied to a distance between atoms i and j given by $d_{ij}$, $h_{(i,j)}^0 = [g_1, g_2, \ldots g_n]$. $g_k$ is represented by equation (7) below.

$$g_k = \frac{1}{\sqrt{2\pi r_{step}}} e^{-\frac{(d_{ij}-r_k)^2}{2r_{step}}}, k=1, 2, \ldots, n \quad (7)$$

In one embodiment, embedding part 402 may mathematically expressed as the following equations (8) and (9).

$$f_a : \text{One-Hot}(\text{type}(\text{atom i})) \rightarrow h_i^0 \quad (8)$$

$$GF : d_{ij} \rightarrow h_{(i,j)}^0 \quad (9)$$

where $f_a$ denotes the neural network that maps the one hot encoding of atom type to $h_i^0$, GF denotes the Gaussian filtering operation. GNN 400 of one embodiment uses a single dense hidden layer for $f_a$.

Message-passing part 404 of GNN 400 may be composed of several message passing layers 410 where at each layer, local messages may be passed between the nodes and edges. Local message passing between the nodes and edges may be defined by equations (10) and (11):

$$\text{Edge to node: } f_v^l : \{h_i^{l-1}, h_{(i,j)}^{l-1} | j \in N_i\} \rightarrow h_i^l \quad (10)$$

$$\text{Node to edge: } f_e^l : \{h_i^l, h_j^l, h_{(i,j)}^{l-1}\} \rightarrow h_{(i,j)}^l \quad (11)$$

where $h_i^l$ is the embedding of node $v_i$ in layer l and $h_{(i,j)}^l$ is the embedding of edge $e_{ij}$, where initial conditions $h_i^0$ and $h_{(i,j)}^0$ are determined in embedding part 402 of GNN 400. $N_i$ denotes a set of indices of neighbor nodes connected to node $v_i$. Message functions $f_v^l$ and $f_e^l$ are node- and edge-specific neural networks that update $h_i^{l-1}$ and $h_{(i,j)}^{l-1}$ to $h_i^l$ and $h_{(i,j)}^l$ respectively. These functions are defined such that after each update (message-passing), embedding $h_i^l$ and $h_{(i,j)}^l$ respectively, better represent the local atomic environment of atom i and the interatomic interactions between atoms i and j. The message functions may be designed flexibly so that they can be altered to emphasize different interatomic dynamics that occur within MD simulations.

In one embodiment, the message functions $f_v^l$ and $f_e^l$ are defined by equations (12) and (13), respectively.

$$f_v^l : h_i^l = g[h_i^{l-1} + \Sigma_{j \in N_i} \sigma((h_i^{l-1} \oplus h_{(i,j)}^{l-1})W_1^l + b_1^l) \odot g \\ ((h_i^{l-1} \oplus h_{(i,j)}^{l-1})W_2^l + b_2^l)] \quad (12)$$

$$f_e^l : h_{(i,j)}^l = g[h_{(i,j)}^{l-1} + \sigma((h_i^l \odot h_j^l)W_3^l + b_3^l) \odot g((h_i^l \odot h_j^l) \\ W_4^l + b_4^l) + \Sigma_{k \in N_j} \sigma((h_i^l \oplus h_j^l \oplus h_k^l \oplus h_{(i,j)}^{l-1} \oplus h_{(k,j)}^{l-1}) \\ W_5^l + b_5^l) \odot g((h_i^l \oplus h_j^l \oplus h_k^l \oplus h_{(i,j)}^{l-1} \oplus h_{(k,j)}^{l-1})W_6^l + \\ b_6^l)] \quad (13)$$

where g denotes a hyperbolic tangent function, σ denotes a sigmoid function, denotes an element wise multiplication operator, and ⊕ denotes a concatenation operator. $W^l$ and $b^l$ represent the weights and biases of the dense hidden layers that compose layer l. The second line of equation (13) represents a three-body function. Equation (12) and the other part of equation (13) represent a two-body function.

Figure 5A:
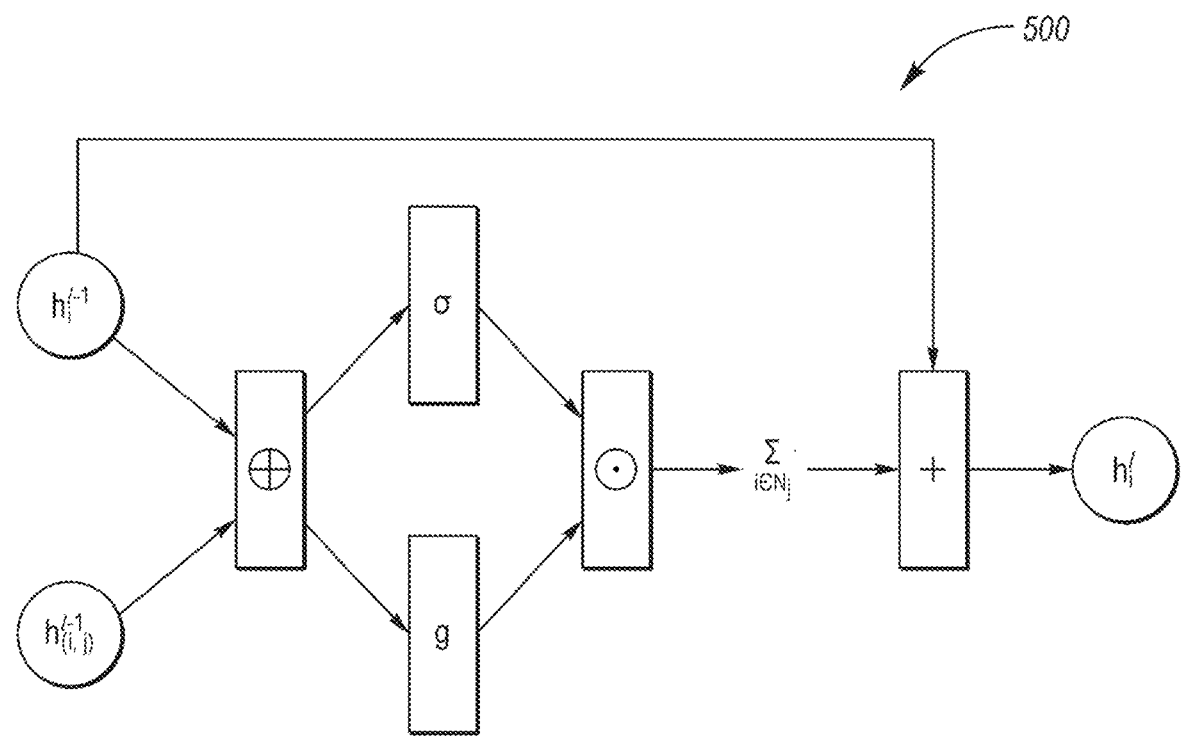
FIGS. 5A and 5B depict schematic views of first and second message functions, respectively, according to one embodiment.
Figure 5B:
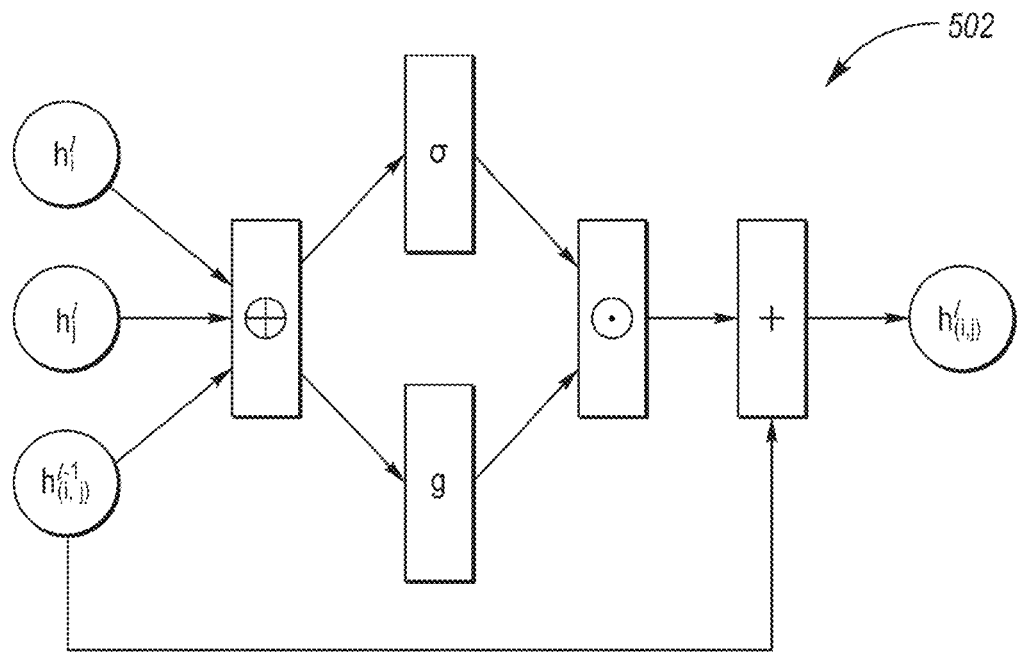
Figures 6A, 6B, 6C, 6D, 6E:
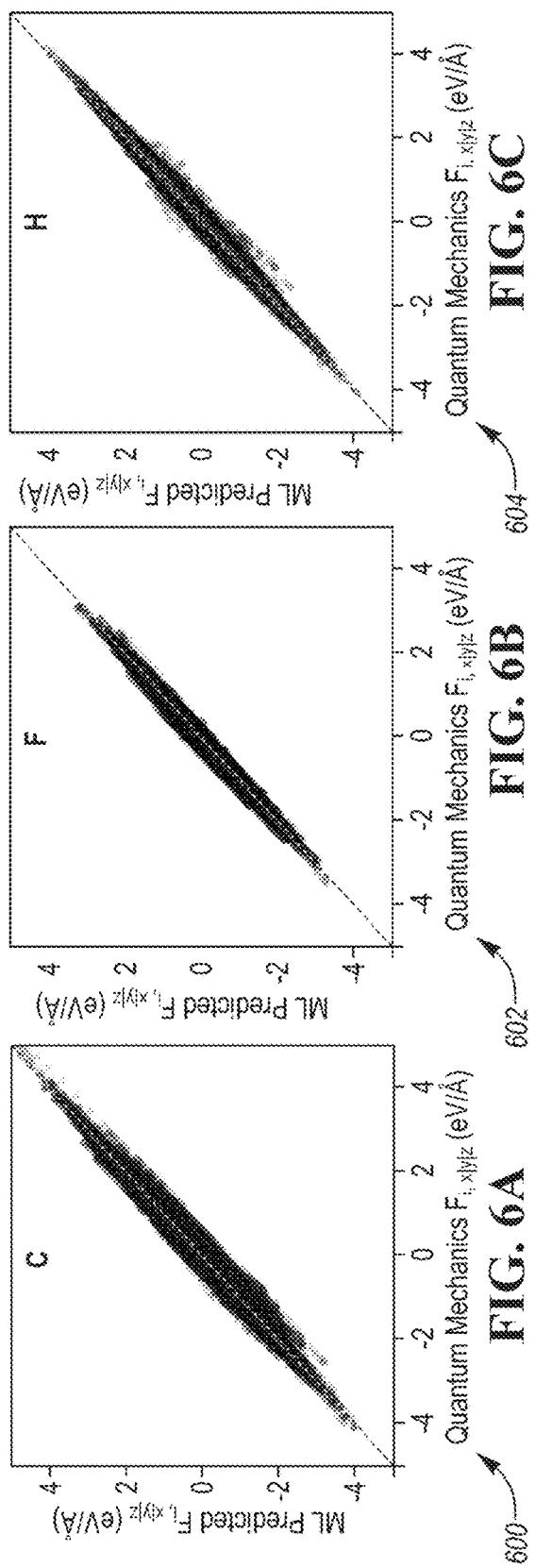
FIGS. 6A through 6E depict graphs showing results of a force prediction of C, F, H, O and S atoms, respectively, taken from a water-Nafion system using a GNN algorithm of one embodiment.
Figure 7A:
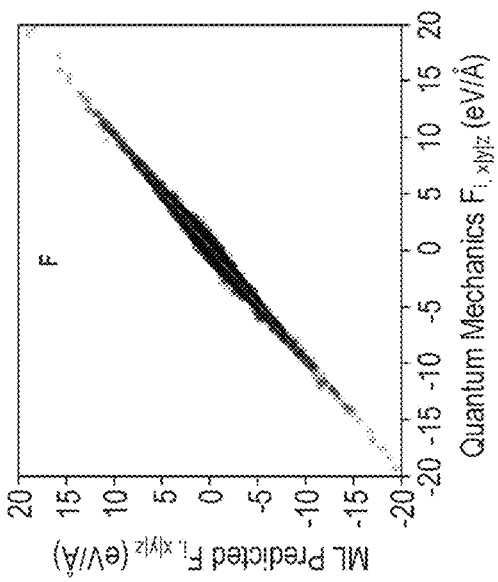
FIGS. 7A through 7D depict graphs showing results of a force prediction of Al, F, H and O atoms, respectively, taken from an $Al_2O_3$ system in which the surface is chemically reacting with HF acid molecules using a GNN algorithm of one embodiment.
Figure 7B:
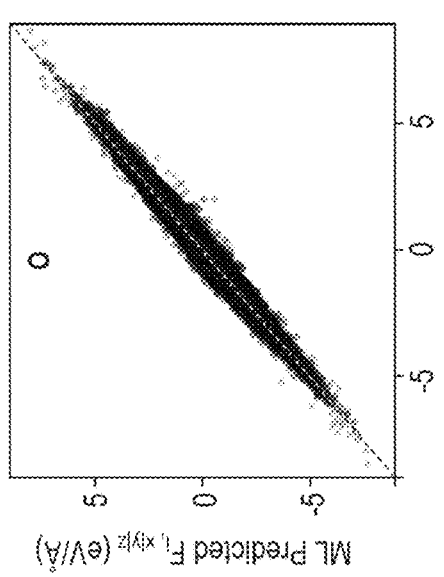
Figure 7C:
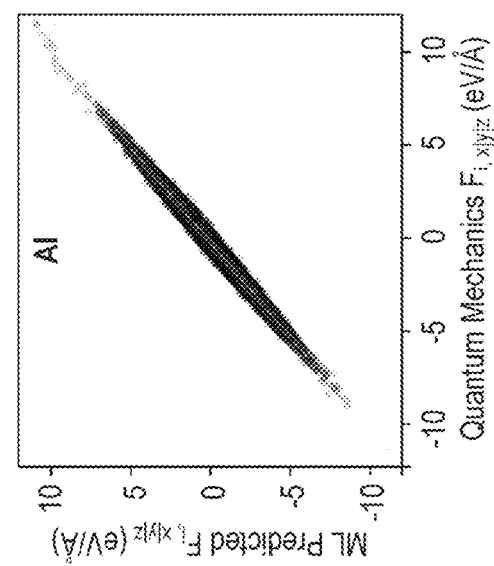
Figure 7D:
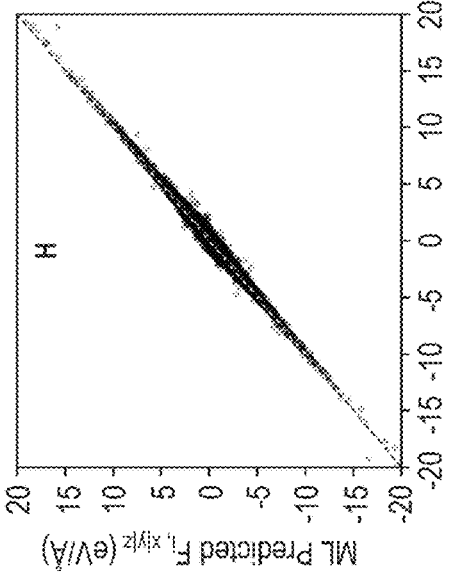

FIGS. 5A and 5B depict schematic views of message functions $f_v^l$ and $f_e^l$ 500 and 502, respectively, according to one embodiment. As shown in FIG. 5A, a concatenation operator ⊕ is applied to $h_i^{l-1}$ and $h_{(i,j)}^{l-1}$, with a hyperbolic tangent function g and a sigmoid function σ applied to the result to obtain two outputs that are fed to an element wise multiplication operator ⊙. These results are summed, as depicted by $\Sigma_{j \in N_i}$. $h_i^{l-1}$ is added to the result to obtain $h_i^l$. As shown in FIG. 5B, a concatenation operator ⊕ is applied to $h_i^l$, $h_j^l$, and $h_{(i,j)}^{l-1}$, with a hyperbolic tangent function g and a sigmoid function σ applied to the result to obtain two outputs that are fed to an element wise multiplication operator ⊙. $h_{(i,j)}^{l-1}$ is added to the result to obtain $h_{(i,j)}^l$. In one embodiment, g denotes a nonlinear activation function.

In force vector calculation part 406, the edge embedding outputs of message-passing part 404 may be used to calculate force vectors for one or more elements within a multi-element system. For a GNN with L message-passing layers, the final state of edge $e_{ij}$ embedding $h_{(i,j)}^L$ may be used to calculate $n_{ij}$, a scalar quantity that denotes the magnitude of the force that atom i is exerting on atom j. The force exerted by atom i on to j is given by $n_{ij} \cdot \vec{u}_{ij}$ and the force prediction of atom j is the sum of forces exerted by neighboring atoms. These calculations may be mathematically represented by equations (14) and (15), reproduced below.

$$f_f : h_{(i,j)}^L \to n_{ij} \quad (14)$$

$$\vec{F}_j = \Sigma_{i \in N_j} n_{ij} \cdot \vec{u}_{ij} \quad (15)$$

where function $f_f$ is a neural network that maps $h_{(i,j)}^L$ to $n_{ij}$ and $\vec{F}_j$ is the force prediction of atom j. GNN 400 of one embodiment may apply a series of 3 dense hidden layers for $f_f$ where the intermediate hidden states are passed through a ReLU activation function.

During the training process of GNN 400, the weights and biases in $f_a$, $f_v^l$, $f_e^l$, and $f_f$ (l=1, 2, . . . , L) are updated through backpropagation to minimize error between the predicted forces and the MD-calculated forces. Under such embodiment, the force field predictions by GNN 400 are translation-invariant, but rotation-covariant to the input atomic coordinates environment $\{\vec{R}_i\}$ of the MD snapshots.

In one embodiment, GNN 400 may be used to directly predict atomic force vectors in an MD simulation for fuel cells, water desalination, catalysis, coating and battery applications. Moreover, GNN 400 of one or more embodiments may be used as part of an MD simulation for drug design and biosciences, including biochemistry design. In one or more embodiments, MD snapshot 300 represented as directed graphs 302 may be composed of nodes, edges and unit vectors. The nodes may be a representation of constituent atoms. The edges may be a representation of interatomic influence between neighboring atoms. The unit vectors may be a representation of the directions of the interatomic influences. The nodes may be initially embedded using, for example, a one hot encoding of atom type. The edges may be initially embedded using, for example, the interatomic distances processed by a Gaussian filter. The initial node and edge embedding may be iteratively updated by iteratively passaging messages from edge to node and node to edge. The messages can be, but are not limited to, functions that are designed to update the node and edge embedding to better represent the local atomic environment and interatomic interactions, respectively. The message passing steps may be conducted more than once. The edge embedding and unit vectors may be used to calculate the interatomic forces between a center atom and its neighboring atoms. The values can be summed to predict the force vector of the center atom.

FIGS. 6A through 6E depict graphs 600, 602, 604, 606 and 608, respectively, showing results of the force prediction of C, F, H, O and S atoms, respectively, taken from a water-Nafion system using a GNN algorithm of one embodiment. Graphs 600, 602, 604, 606 and 608 plot GNN predicted $F_{i,x|y|z}$ as a function of $F_{i,x|y|z}$ calculated from a quantum mechanics density functional theory (DFT) simulation. $F_{i,x|y|z}$ denotes the projection of $\vec{F}_i$ onto the Cartesian x, y and z axes. The following error equation (16) may be used to calculate the average error of the GNN algorithm calculation method:

$$\sqrt{\langle |\vec{F}_{i,GNN} - \vec{F}_{i,QM}|^2 \rangle} \quad (16)$$

Using the error equation set forth above, the error between the GNN algorithm and the quantum mechanics DFT simulation is 0.273 eV/A, 0.159 eV/A, 0.148 eV/A, 0.221 eV/A, and 0.340 eV/A for the prediction of C, F, H, O and S atoms, respectively, which is within an acceptable range. In these examples, no samples from the test set were seen during the training cycle.

FIGS. 7A through 7D depict graphs 700, 702, 704 and 706, respectively, showing results of the force prediction of Al, F, H and O atoms, respectively, taken from an $Al_2O_3$ system in which the surface is chemically reacting with HF acid molecules using a GNN algorithm of one embodiment. Graphs 700, 702, 704 and 706 plot GNN predicted $F_{i,x|y|z}$ as a function of $F_{i,x|y|z}$ calculated from a quantum mechanics DFT simulation. Using the error equation set forth above, the error between the GNN algorithm and the quantum mechanics DFT simulation is 0.297 eV/A, 0.274 eV/A, 0.282 eV/A, and 0.295 eV/A for the prediction of Al, F, H and O atoms, respectively, which is within an acceptable range. In these examples, no samples from the test set were seen during the training cycle.

Figure 8A:
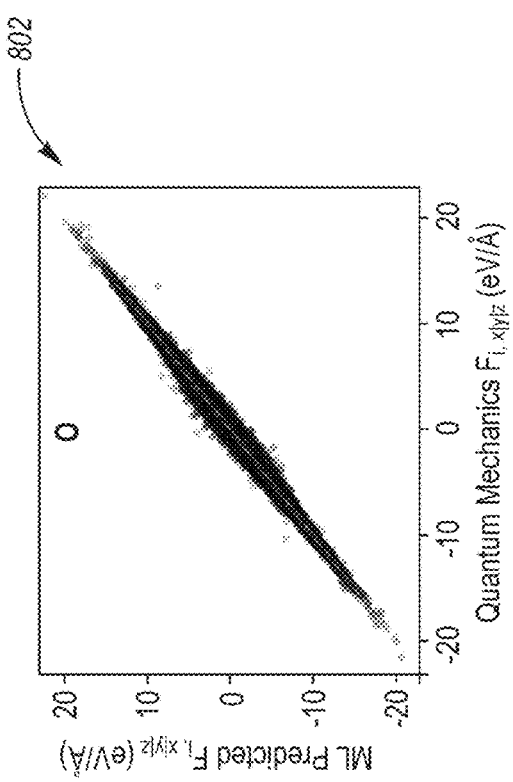
FIGS. 8A through 8C depict graphs showing results of a force prediction of Li, O and P atoms, respectively, taken from an $Li_4P_2O_7$ system using a GNN algorithm of one embodiment.
Figure 8B:
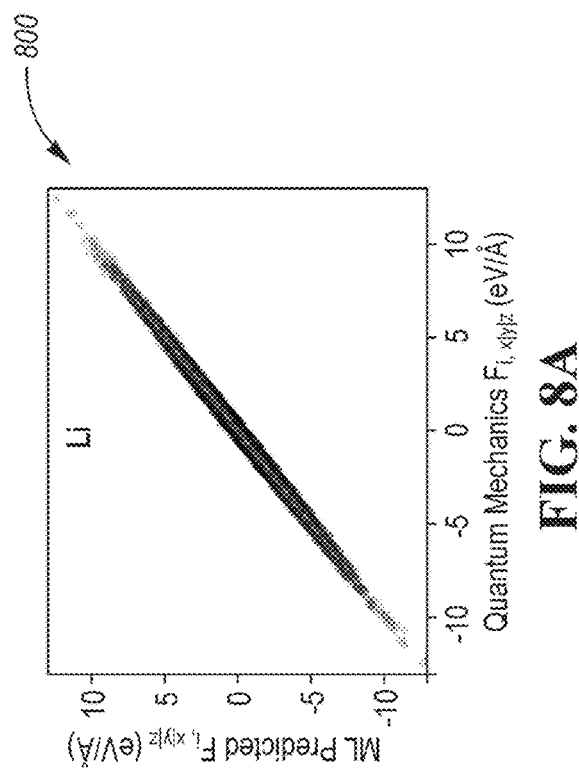
Figure 8C:
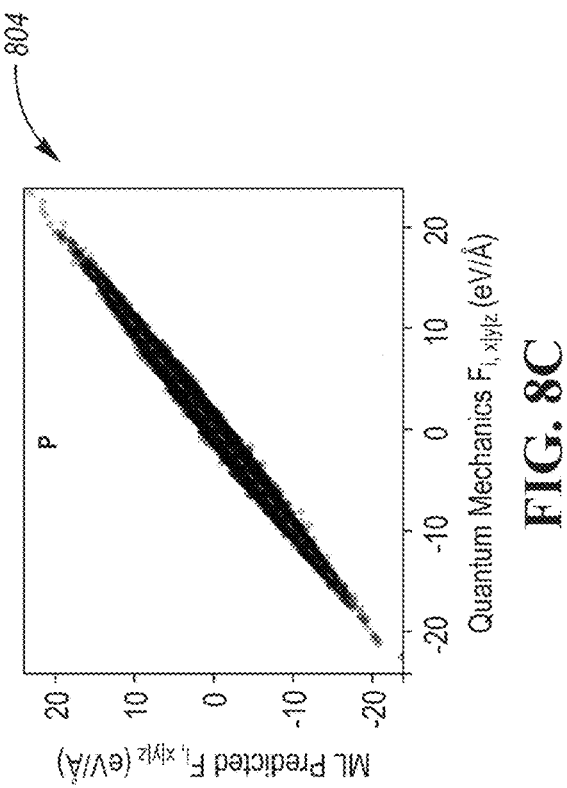

FIGS. 8A through 8C depict graphs 800, 802 and 804, respectively, showing results of the force prediction of Li, 0 and P atoms, respectively, taken from an $Li_4P_2O_7$ system using a GNN algorithm of one embodiment. Graphs 800, 802 and 804 plot GNN predicted $F_{i,x|y|z}$ as a function of $F_{i,x|y|z}$ calculated from a quantum mechanics DFT simulation. Using the error equation set forth above, the error between the GNN algorithm and the quantum mechanics DFT simulation is 0.238 eV/A, 0.419 eV/A, and 0.683 eV/A for the prediction of Li, O and P atoms, respectively, which is within an acceptable range. In these examples, no samples from the test set were seen during the training cycle.

Figure 9:
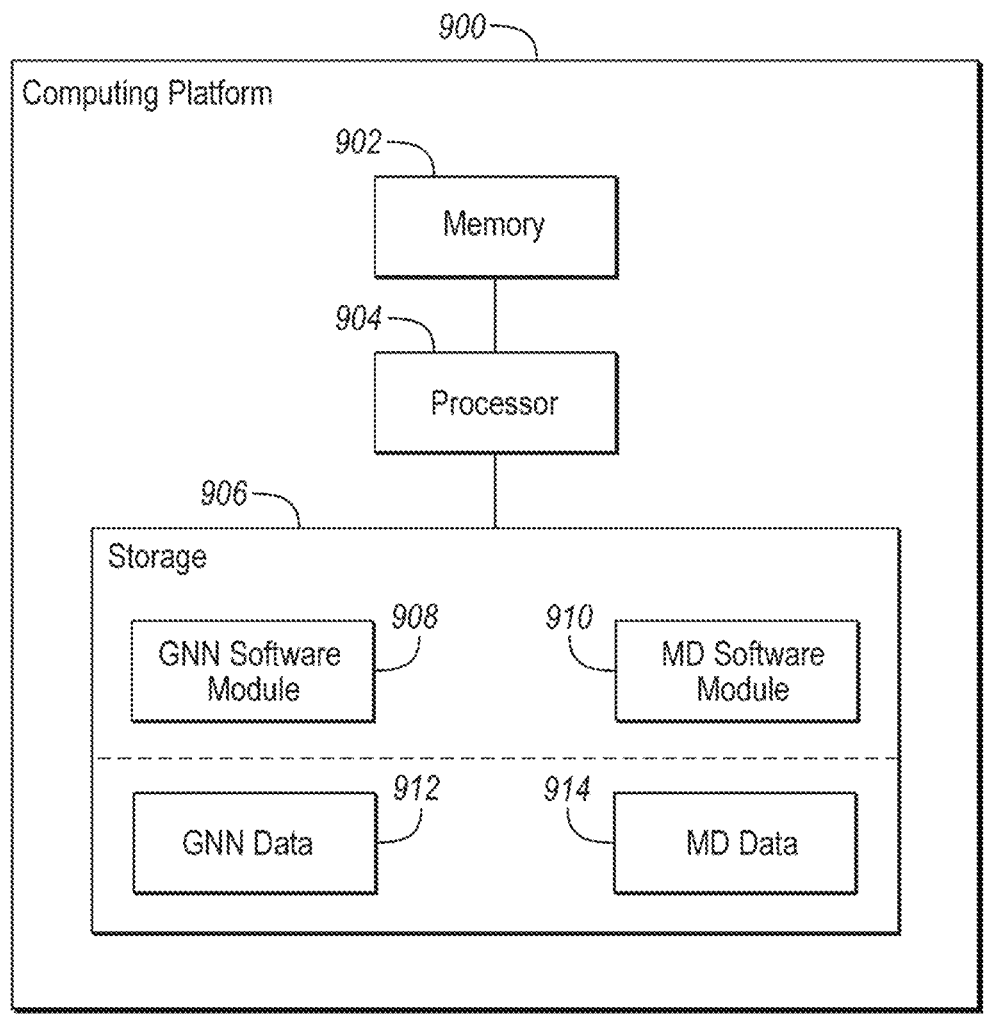
FIG. 9 is a schematic diagram of a computing platform that may be utilized to implement the GNN algorithms in one or more embodiment, for instance, the GNN algorithm of FIG. 4.

The GNN algorithms and/or methodologies of one or more embodiments are implemented using a computing platform, such as the computing platform 900 illustrated in FIG. 9. The computing platform 900 may include memory 902, processor 904, and non-volatile storage 906. The processor 904 may include one or more devices selected from high-performance computing (HPC) systems including high-performance cores, microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on computer-executable instructions residing in memory 902. The memory 902 may include a single memory device or a number of memory devices including, but not limited to, random access memory (RAM), volatile memory, non-volatile memory, static random access memory (SRAM), dynamic random access memory (DRAM), flash memory, cache memory, or any other device capable of storing information. The non-volatile storage 906 may include one or more persistent data storage devices such as a hard drive, optical drive, tape drive, non-volatile solid state device, cloud storage or any other device capable of persistently storing information.

The processor 904 may be configured to read into memory 902 and execute computer-executable instructions residing in GNN software module 908 of the non-volatile storage 906 and embodying GNN algorithms and/or methodologies of one or more embodiments. The processor 904 may be further configured to read into memory 902 and execute computer-executable instructions residing in MD software module 910 (such as LAMMPS) of the non-volatile storage 906 and embodying MD algorithms and/or methodologies. The software modules 908 and 910 may include operating systems and applications. The software modules 908 and 910 may be compiled or interpreted from computer programs created using a variety of programming languages and/or technologies, including, without limitation, and either alone or in combination, Java, C, C++, C #, Objective C, Fortran, Pascal, Java Script, Python, Perl, and PL/SQL. In one embodiment, PyTorch, which is a package for the Python programming language, may be used to implement code for the GNNs of one or more embodiments. The code framework may be based on a crystal graph convolutional neural network (CGCNN) code, which is available under license from the Massachusetts Institute of Technology of Cambridge, Massachusetts.

Upon execution by the processor 904, the computer-executable instructions of the GNN software module 908 and the MD software module 910 may cause the computing platform 900 to implement one or more of the GNN algorithms and/or methodologies and MD algorithms and/or methodologies, respectively, disclosed herein. The non-volatile storage 906 may also include GNN data 912 and MD data 914 supporting the functions, features, and processes of the one or more embodiments described herein.

The program code embodying the algorithms and/or methodologies described herein is capable of being individually or collectively distributed as a program product in a variety of different forms. The program code may be distributed using a computer readable storage medium having computer readable program instructions thereon for causing a processor to carry out aspects of one or more embodiments. Computer readable storage media, which is inherently non-transitory, may include volatile and non-volatile, and removable and non-removable tangible media implemented in any method or technology for storage of information, such as computer-readable instructions, data structures, program modules, or other data. Computer readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. Computer readable program instructions may be downloaded to a computer, another type of programmable data processing apparatus, or another device from a computer readable storage medium or to an external computer or external storage device via a network.

Computer readable program instructions stored in a computer readable medium may be used to direct a computer, other types of programmable data processing apparatus, or other devices to function in a particular manner, such that the instructions stored in the computer readable medium produce an article of manufacture including instructions that implement the functions, acts, and/or operations specified in the flowcharts or diagrams. In certain alternative embodiments, the functions, acts, and/or operations specified in the flowcharts and diagrams may be re-ordered, processed serially, and/or processed concurrently consistent with one or more embodiments. Moreover, any of the flowcharts and/or diagrams may include more or fewer nodes or blocks than those illustrated consistent with one or more embodiments.

While all of the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the general inventive concept.

What is claimed is:

1. A computational method for simulating motion of elements within a multi-element system using a graph neural network (GNN), the computational method comprising:
    converting a molecular dynamics snapshot of the elements within the multi-element system into a directed graph comprised of nodes and edges, the nodes including first and second nodes and the edges including first and second edges;
    initially embedding the nodes and the edges to obtain initially embedded nodes and edges;
    updating the initially embedded nodes and edges by passing a first message from the first edge to the first node using a first message function and passing a second message from the first node to the first edge using a second message function to obtain updated embedded nodes and edges, the first message function uses the first message and the initially embedded nodes as inputs, the first message function concatenates the initially embedded nodes, with a hyperbolic tangent function and a sigmoid function applied to the result to obtain first and second outputs;
    predicting a force vector for one or more elements within the multi-element system based on the updated embedded edges and a unit vector pointing from the first node to the second node or the second node to the first node; and
    training the GNN to update weights and biases through backpropagation to extract one or more rotationally-invariant features from the molecular dynamics snapshot to predict atomic forces to reduce error between the predicted forces and the molecular dynamics calculated forces.

2. The computational method of claim 1, wherein the initially embedding step includes initially embedding the edges using a Gaussian filter to obtain the initially embedded edges.

3. The computational method of claim 1, wherein the first message function includes feeding the first and second outputs to an element wise multiplication operator.

4. The computational method of claim 1, wherein the computational method is integrated into molecular dynamics (MD) software.

5. The computational method of claim 1, wherein the first and second nodes represent first and second neighboring atoms and the first and second edges represent interatomic influences between the first and second neighboring atoms.

6. The computational method of claim 5, wherein the unit vector is a representation of a direction of the interatomic influences between the first and second neighboring atoms.

7. The computational method of claim 5, wherein the initially embedding step includes mapping the nodes using a unique representation of an atom's element to obtain initially embedded nodes.

8. The computational method of claim 6, wherein a single dense hidden layer is used for a unique representation of an atom's element.

9. A computational method for simulating motion of elements within a multi-element system using a graph neural network (GNN), the computational method comprising:
    converting a molecular dynamics snapshot of the elements within the multi-element system into a directed graph comprised of nodes and edges, the nodes including first, second and third nodes and the edges including first, second and third edges;

initially embedding the nodes and the edges to obtain initially embedded nodes and edges;

updating the initially embedded nodes and edges by passing a first message from the first edge to the first node using a first message function and passing a second message from the first node to the first edge using a second message function to obtain updated embedded nodes and edges, the second message function representing interactions between the first, second and third nodes, the second message function uses the second message function and the initially embedded edges as inputs, the second message function concatenates the initially embedded edges, with a hyperbolic tangent function and a sigmoid function applied to the result to obtain first and second outputs;

predicting a force vector for one or more elements within the multi-element system based on the updated embedded edges; and training the GNN to update weights and biases through backpropagation to extract one or more rotationally-invariant features from the molecular dynamics snapshot to predict atomic forces to reduce error between the predicted forces and the molecular dynamics calculated forces.

10. The computational method of claim 9, wherein the initially embedding step includes initially embedding the edges using a Gaussian filter to obtain the initially embedded edges.

11. The computational method of claim 9, wherein the second message function includes feeding the first and second outputs to an element wise multiplication operator.

12. The computational method of claim 9, wherein the computational method is integrated into molecular dynamics (MD) software.

13. The computational method of claim 9, wherein the first and second nodes represent first and second neighboring atoms and the first and second edges represent interatomic influences between the first and second neighboring atoms.

14. The computational method of claim 13, wherein the initially embedding step includes mapping the nodes using a unique representation of an atom's element to obtain the initially embedded nodes, and a single dense hidden layer is used for the unique representation of the atom's element.

15. A computational method for simulating motion of elements within a multi-element system using a graph neural network (GNN), the computational method comprising:

converting a molecular dynamics snapshot of the elements within the multi-element system into a directed graph comprised of nodes and edges, the nodes including first and second nodes and the edges including first and second edges;

initially embedding the nodes and the edges to obtain initially embedded nodes and edges;

updating the initially embedded nodes and edges by iteratively passing a first message from the first edge to the first node using a first message function and iteratively passing a second message from the first node to the first edge using a second message function to obtain updated embedded nodes and edges, the first message function uses the first message and the initially embedded nodes as inputs, the first message function concatenates the initially embedded nodes, with a nonlinear activation function applied to the result;

predicting a force vector for one or more elements within the multi-element system based on the updated embedded edges; and training the GNN to update weights and biases through backpropagation to extract one or more rotationally-invariant features from the molecular dynamics snapshot to predict atomic forces to reduce error between the predicted forces and the molecular dynamics calculated forces.

16. The computational method of claim 15, wherein the iteratively passing steps of the updating step are conducted more than once.

17. The computational method of claim 15, wherein the nonlinear activation function is a ReLU activation function.

18. The computational method of claim 15, wherein the computational method is integrated into molecular dynamics (MD) software.

19. The computational method of claim 15, wherein the first and second nodes represent first and second neighboring atoms and the first and second edges represent interatomic influences between the first and second neighboring atoms.

20. The computational method of claim 19, wherein the initially embedding step includes mapping the nodes using a unique representation of an atom's element to obtain initially embedded nodes, and a single dense hidden layer is used for the unique representation of an atom's element.

* * * * *